United States Patent
Lal et al.

(12) 
(10) Patent No.: US 6,610,526 B2
(45) Date of Patent: *Aug. 26, 2003

(54) HUMAN E1-LIKE PROTEIN

(75) Inventors: Preeti Lal, Santa Clara, CA (US); Neil C. Corley, Mountain View, CA (US); Henry Yue, Sunnyvale, CA (US)

(73) Assignee: Inctye Corporation, Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 16 days.

(21) Appl. No.: 09/039,064

(22) Filed: Mar. 13, 1998

(65) Prior Publication Data

US 2002/0086379 A1 Jul. 4, 2002

(51) Int. Cl.[7] ............... C12Q 1/68; C12P 21/06; C12N 9/00; C12N 9/50; C07H 21/04
(52) U.S. Cl. ............ 435/219; 435/6; 435/69.1; 435/183; 435/252.3; 435/320.1; 435/325; 536/23.2; 536/23.4; 536/23.5
(58) Field of Search ............... 435/69.1, 183, 435/219, 6, 252.3, 320.1, 325; 536/23.2, 23.4, 23.5

(56) References Cited

PUBLICATIONS

GenBank Accession No. N99449 (Hillier et al.), Apr. 12, 1996.*
EST Database Accession No. AA311634 (Adams et al.), Apr. 19, 1997.*
GenBank Accession No. AA780421, Hillier et al. Feb. 5, 1998.*
GenBank Accession No. H08013, Hillier et al. Jun. 23, 1995.*

* cited by examiner

*Primary Examiner*—Rebecca E. Prouty
*Assistant Examiner*—Manjunath N. Rao
(74) *Attorney, Agent, or Firm*—Incyte Corporation

(57) ABSTRACT

The invention provides a human E1-like protein (HELPR) and polynucleotides which identify and encode HELPR. The invention also provides expression vectors, host cells, antibodies, agonists, and antagonists. The invention also provides methods for treating or preventing disorders associated with expression of HELPR.

10 Claims, 8 Drawing Sheets

```
                        11          20          29       38          47       56
5' AACAA TAT GGC GGA CGA GGA GCG GAG AAG AAA AGA AGA ATA GAG GAG CTG 65          74          83       92          101      110
   CTG GCT GAG AAA ATG GCT GTT GAT GGT GGG TGT GGG GAC ACT GGA GAC TGG GAA
              M   A   V   D   G   G   C   G   D   T   G   D   W   E 119         128         137      146         155      164
   GGT CGC TGG AAC CAT GTA AAG AAG TTC CTC GAG TCT CGA TCT GAA CCC TTC ACA CAC
   G   R   W   N   H   V   K   K   F   L   E   S   R   S   P   F   T   H 173         182         191      200         209      218
   CCT GAT TTC GAA CCG AGC ACT GAA TCT CTC CAG TTG TTA GAT ACA TGT AAA
   P   D   F   E   P   S   T   E   S   L   Q   F   L   L   D   T   C   K 227         236         245      254         263      272
   GTT CTA GTC ATT GGA GCT GGC GGC TTA GGA TGT GAG CTC CTG AAA AAT CTG GCC
   V   L   V   I   G   A   G   G   L   G   C   E   L   L   K   N   L   A 281         290         299      308         317      326
   TTG TCT GGT TTT AGA CAG ATT CAT GTT ATA GAT ATG GAC ACT ATA GAT GTT TCC
   L   S   G   F   R   Q   I   H   V   I   D   M   D   T   I   D   V   S 335         344         353      362         371      380
   AAT CTA AAT AGG CAG TTT TTA TTT AGG CCT AAA GAT ATT GGA AGA CCT AAG GCT
   N   L   N   R   Q   F   L   F   R   P   K   D   I   G   R   P   K   A

FIGURE 1A
```

```
              389       398       407       416       425       434
    GAA GTT GCT GCA GAA TTT CTA AAT GAC AGA GTT CCT AAT TGC AAT GTA GTT CCA
     E   V   A   A   E   F   L   N   D   R   V   P   N   C   N   V   V   P 443       452       461       470       479       488
    CAT TTC AAC AAG ATT CAA GAT TTT AAC GAC ACT TTC TAT CGA CAA TTT CAT ATT
     H   F   N   K   I   Q   D   F   N   D   T   F   Y   R   Q   F   H   I 497       506       515       524       533       542
    ATT GTA TGT GGA CTG GAC TCT ATC GCC AGA AGA TGG ATA AAT GGC ATG CTG
     I   V   C   G   L   D   S   I   A   R   R   W   I   N   G   M   L 551       560       569       578       587       596
    ATA TCT CTT CTA AAT TAT GAA GAT GGT GTC TTA GAT CCA AGC TCC ATT GTC CCT
     I   S   L   L   N   Y   E   D   G   V   L   D   P   S   S   I   V   P 605       614       623       632       641       650
    TTG ATA GAC GGG GGG ACA GAA GGT TTT AAA GGA AAT GCC CGG GTG ATT CTG CCT
     L   I   D   G   G   T   E   G   F   K   G   N   A   R   V   I   L   P 659       668       677       686       695       704
    GGA ATG ACT GCT TGT ATC GAA CTG ACG CTG GAA CTT TAT CCA CCA CAG GTT AAT
     G   M   T   A   C   I   E   L   T   L   E   L   Y   P   P   Q   V   N 713       722       731       740       749       758
    TTT CCC ATG TGC ACC ATT GCA TCT ATG CCC AGG CTA CCA GAA CAC TGT ATT GAG
     F   P   M   C   T   I   A   S   M   P   R   L   P   E   H   C   I   E

```
767                 776             785             794             803             812
TAT GTA AGG ATG TTG CAG TGG CCT AAG GAG CAG TTT GGA GAA GGG GTT CCA
 Y   V   R   M   L   Q   W   P   K   E   Q   F   G   E   G   V   P 821             830             839             848             857             866
TTA GAT GGA GAT GAT CCT GAA CAT ATA CAA TGG ATT TTC CAA AAA TCC CTA GAG
 L   D   G   D   D   P   E   H   I   Q   W   I   F   Q   K   S   L   E 875             884             893             902             911             920
AGA GCA TCA CAA TAT AAT ATT AGG GGT GTT ACG TCC ACA GTC CTC ACT CAA GGG GTA
 R   A   S   Q   Y   N   I   R   G   V   T   S   T   V   L   T   Q   G   V 929             938             947             956             965             974
AGA ATC ATT CCT GCA GTA TCC ACA AAT GCA ATT AGG CTC ATT GCA GCT GTG
 R   I   I   P   A   V   S   T   N   A   I   R   L   I   A   A   V 983             992             1001            1010            1019            1028
ACT GAG GTT TTT AAA ATA GCC ACA AGT GCA TAC ATT CCC TTG AAT AAT
 T   E   V   F   K   I   A   T   S   A   Y   I   P   L   N   N 1037            1046            1055            1064            1073            1082
TGT GCC ACT GAG GTT TTT AAT GAT GTA GAT GGG CTG TAT ACA TAC ACA TTT GAA GCA GAA
 C   A   T   E   V   F   N   D   V   D   G   L   Y   T   Y   T   F   E   A   E 1091            1100            1109            1118            1127            1136
AGA AAG GTT AGT AGT ATT AAG AAC ACA TTT TTG ATC ATG CAT ATT TTG ATT TTT
 R   K   V   S   S   I   K   N   T   F   L   I   M   H   I   L   I   F
```

```
      1145          1154         1163         1172         1181          1190
AAA TAT TAT TGG TTA GAA ATT TGA ACA AAG TCA CCC ATA CAT TTT CTA ACT TCC
 K   Y   Y   W   L   E   I 1199          1208         1217         1226         1235          1244
AGA ACT CTA CTT ATT ATA TAT CTT TTG CTT TAT AGC CTG AAA TAA CTC TAT AGC 1253          1262         1271         1280         1289          1298
GAA GTA ATT TAC AAG AAA TGG TCT ATT ATG AAA AGC AGG CTT TAA AGC ATA AAA 1307          1316         1325         1334         1343          1352
ATT TTT TTA TAG GAA ATA TGC ATG ATT ATA AAA CAA CCT GAT TTT TAT TTT ATT 1361          1370         1379         1388         1397          1406
GTT CAT AAA AGA GAC TAA TAT TGG TGC ATG TGC TGT AAT TTG TTG TGT ATT 1415          1424         1433         1442         1451          1460
ATG TGT GTA GGA AAA CTG CCC AGC TTG TAG CCA GCT TCC TCA AAA TAT TCA GTT 1469          1478         1487         1496         1505          1514
TTC TCC ATC AGC TAA ACT ACA GGA GGT TTT GGA TTA TCT AAC CAA TAG TGC TTC 1523          1532         1541         1550         1559          1568
TCT GTA AGT ATT GTA GAT TTT TGT TAT GTT GTA AAA ATC ATT TTT GTG ATT TTT 1577          1586         1595         1604         1613          1622
GAA ACC TTA AAA AAA TTA TCT TTT GAT AAA AAT TAT GTT TGA TAC TTC TCT CTC
```

FIGURE 1D

```
1631       1640       1649       1658       1667       1676
ATC ATA ATC TTT AGG CAA ATG AAA TCT CCA GCC ATC ACA GCC ACC CTA GAG GGA 1685       1694       1703       1712       1721       1730
AAA AAT AGA ACA CTT TAC TTA CAG GTT ATC AAT GTG TAT TTT AAA TTT TTT TCA 1739       1748       1757       1766       1775       1784
GAA AAT TAT ATC AAG TTT TAT TTT ACT TTA ATG TGT CTT ACA TTA AAG TAA TTT 1793       1802       1811       1820       1829       1838
TGT TTT CTA GTC GGT AAC CTC TAT TGA AGA ACG AAC AAG GCC AAA TCT CTC CAA 1847       1856       1865       1874       1883       1892
AAC ATT GAA AGG TAT TTT ACA TAA GGG TAT TTA CTA ATC ATT TTC TTT CTT TTC 1901       1910       1919       1928       1937       1946
TCT CTT TTT GGT GAA AGT AAT CAG TGC TTG TTC TAG ATT TCC TCT TAA TGC CTT 1955       1964       1973       1982       1991       2000
GTA TAT GGT CAG GTA ATA ATT ACT TAC AAC TTT AGA CAT ATT AAT AGA ATT AAT 2009       2018       2027       2036       2045       2054
TGC TCT TTT AGT AGG ATA TTT AAA ATC TCC AAG GAA TCA ATA TTT ACT TTG ATT 2063       2072       2081
AAA GAG GAT TGG NTT TTG ATG TTT TNC TAG  3'
```

```
319 NNYLVFNDVDGLYT--------------          2546462
320 DNYLNFTQIHGAYTSVVSMMKDDNCLTCSG         GI 1055197

333 --YTFEA---------ERKVSSIKNTFLIMHIL      2546462
350 GRLPFEVSPSSTLESLIRLSERFHLKHPT          GI 1055197

355 IF---KYY----------------               2546462
380 LATSTRKLYCISSFMPQFEQESKENLHTSM         GI 1055197

360 ------------WLE-IH                     2546462
410 KDLVSDGEEILVSDEALSRALTLRIQLI           GI 1055197
```

FIGURE 2C

HUMAN E1-LIKE PROTEIN

FIELD OF THE INVENTION

This invention relates to nucleic acid and amino acid sequences of a human E1-like protein and to the use of these sequences in the diagnosis, treatment, and prevention of cell proliferative, immunological, neurological, and reproductive disorders.

BACKGROUND OF THE INVENTION

The ubiquitin conjugation system (UCS) plays a major role in the selective degradation of cellular proteins in eukaryotes. UCS targets abnormal proteins for destruction and regulates the turn-over of proteins that control gene expression and cell cycle progression. For example, UCS mediates the degradation of mitotic cyclins, oncoproteins, tumor suppressors, viral proteins, transcription factors, and cell surface receptors. The timed destruction of these regulatory proteins by UCS is critical for ensuring normal cellular function. (Ciechanover, A. (1994) Cell 79:13–21; and Rolfe, M. et al. (1997) J. Mol. Med. 75:5–17.)

Ubiquitin (Ub) conjugation and protein degradation occur in several steps. (Jentsch, S. (1992) Annu. Rev. Genet. 26:179–207). First, Ub, a small, abundant protein, is activated by ubiquitin-activating enzyme (E1) in an ATP-dependent reaction. This reaction joins the C-terminus of Ub to the thiol group of a cysteine residue in E1. The product of this reaction is a high-energy E1-Ub thiolester intermediate. In a similar reaction, Ub is subsequently transferred from E1 to one of several Ub-conjugating enzymes (E2). Ub is then transferred from E2 in a reaction that joins the C-terminal glycine of Ub to an internal lysine of a protein targeted for destruction. In most cases, multiple ubiquitin moieties are transferred to the target protein. In some instances, additional factors called ubiquitin-ligases (E3) are required for target recognition. The ubiquitinated protein is then degraded by the proteasome, a large complex of up to 20 proteases and accessory factors. Following degradation of the target protein, Ub is released and reutilized.

Modifications of this pathway occur primarily in the steps involving E2 activity. A large number of structurally related, yet functionally distinct E2 enzymes have been identified across species. (Jentsch, supra.) These enzymes operate in distinct cellular compartments on specific target proteins, suggesting that E2 determines the selectivity of protein degradation.

E1 structure and function are conserved among various species including mammals, such as human and mouse; lower eukaryotes, such as yeast and nematode; and plants, such as wheat and wall cress. (Jentsch, supra; and Wilson, R. et al. (1994) Nature 368:32–38.) E1 is about 100 kilodaltons and contains an ATP-binding consensus sequence and an active site consensus sequence which includes the key cysteine residue to which Ub joins. No more than two different E1 proteins have been identified in a single species, suggesting that the general mechanism of Ub activation is common to all UCS pathways. However, in budding yeast, two E1 enzymes, Uba1p and Uba2p, have been identified, and both are essential for yeast viability, suggesting that these two proteins have distinct, nonoverlapping functions. (Dohmen, R. J. et al. (1995) J. Biol. Chem. 270:18099–18109.)

Although E2 appears to play the primary role in determining the activity of its cognate UCS, localization and modification of E1 may also influence this activity. For example, human E1 exists as two isoforms, E1a and E1b. E1a is localized primarily to the nucleus, while E1b is localized to the cytoplasm. E1a exists predominantly in a phosphorylated form, while E1b is mainly nonphosphorylated. The first 11 amino acids of E1a contain a phosphoserine at residue 4 and a nuclear localization signal immediately following. Nuclear localization is required for phosphorylation, indicating that phosphorylation occurs within the nucleus itself. (Stephen, A. G. et al. (1997) J. Biol. Chem. 272:10895–10903.) Additional evidence suggests that the mitosis-specific kinase $p34^{cdc2}$ may phosphorylate E1a in a cell cycle dependent manner. (Nagai, Y. et al. (1995) J. Cell Sci. 108:2145–2152.)

The diverse and complex roles of UCS have been elucidated using mutant mammalian cell lines that contain thermolabile E1. For example, the mouse cell line ts85 arrests in G2 phase of the cell cycle, suggesting that E1 activates Ub in a pathway required for cell cycle progression. (Jentsch, supra.) The CHO hamster cell line, ts20, is defective in the maturation of autophagic vacuoles which degrade proteins and subcellular organelles in response to stress conditions. (Lenk, S. E. et al. (1992) J. Cell Biol. 301–108.) In addition, mouse L-cells are defective in DNA replication, and this defect is rescued by either human or mouse E1 encoded by the A1S9 gene. Interestingly, A1S9 maps to a region of the mouse Y chromosome that is involved in spermatogenesis, and A1S9 is expressed in testis, suggesting that E1 encoded by A1S9 may play a specialized role in DNA replication events that occur during spermatogenesis. (Kay, G. F. et al (1991) Nature 354:486–489.)

UCS has been implicated in the molecular mechanisms and pathology of various diseases, and elements of UCS are therefore likely targets for therapeutic intervention. For example, agents that block UCS may allow the persistence of molecules that control cell proliferation. One such molecule is the tumor suppressor protein, p53, which is normally degraded by UCS. Inhibition of p53 degradation may prevent tumor cell proliferation. Likewise, inhibitors of mitotic cyclin degradation would also prevent cell cycle progression. (Rolfe et al. supra.) Another application for therapies that target UCS is in the treatment of immune disorders. For example, UCS mediates the proteolytic activation of NF-κB, a key transcriptional regulator of genes involved in the immune response. Different therapeutic strategies that target this activation step could either stimulate the immune response or suppress autoimmune or inflammatory disorders. (Ciechanover, supra.) Finally, agents that block UCS may be valuable in the treatment of neurodegenerative disorders such as Alzheimer's disease, in which abnormally high levels of ubiquitin and ubiquitin-conjugated proteins are observed in diseased tissue. (Muller, S. and Schwartz, L. M. (1995) Bioessays 17:677–684.) In fact, an E1-like protein, APP-BP1, has been found that specifically binds to β-amyloid precursor protein. This protein is processed to form β-amyloid, a major component of the plaque-like deposits that characterize Alzheimer's brain pathology. (Chow, N. et al. (1996) J. Biol. Chem. 271:11339–11346.)

The discovery of a new human E1-like protein and the polynucleotides encoding it satisfies a need in the art by providing new compositions which are useful in the diagnosis, treatment, and prevention of cell proliferative, immunological, neurological, and reproductive disorders.

SUMMARY OF THE INVENTION

The invention is based on the discovery of a new human E1-like protein (HELPR), the polynucleotides encoding HELPR, and the use of these compositions for the diagnosis, treatment, or prevention of cell proliferative, immunological, neurological, and reproductive disorders. The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1.

The invention also includes an isolated and purified polynucleotide variant having at least 90% polynucleotide sequence identity to the polynucleotide encoding the polypeptide comprising the amino acid sequence of SEQ ID NO:1 or a fragment of SEQ ID NO:1.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 90% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a cell proliferative disorder, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing an immunological disorder associated with decreased expression or activity of HELPR, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing an immunological disorder associated with increased expression or activity of HELPR, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing a neurological disorder, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing a reproductive disorder, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of HELPR. The alignment was produced using MacDNASIS PRO™ software (Hitachi Software Engineering Co. Ltd., San Bruno, Calif.).

FIGS. 2A, 2B, and 2C show the amino acid sequence alignments among HELPR (2546462; SEQ ID NO:1), nematode CESAB54F (GI 1055197; SEQ ID NO:3), and yeast Uba2p (GI 793879; SEQ ID NO:4), produced using the multisequence alignment program of LASERGENE™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HELPR," as used herein, refers to the amino acid sequences of substantially purified HELPR obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HELPR, increases or prolongs the duration of the effect of HELPR. Agonists may include proteins, nucleic acids, carbohydrates, or any other molecules which bind to and modulate the effect of HELPR.

An "allele" or an "allelic sequence," as these terms are used herein, is an alternative form of the gene encoding HELPR. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HELPR, as described herein, include those sequences with deletions, insertions, or substitutions of different nucleotides, resulting in a polynucleotide the same HELPR or a polypeptide with at least one functional characteristic of HELPR. Included within this definition are polymorphisms which may or may not be readily detectable using a particular oligonucleotide probe of the polynucleotide encoding HELPR, and improper or unexpected hybridization to alleles, with a locus other than the normal chromosomal locus for the polynucleotide sequence encoding HELPR. The encoded protein may also be "altered," and may contain deletions, insertions, or substitutions of amino acid residues which produce a silent change and result in a functionally equivalent HELPR. Deliberate amino acid substitutions may be made on the basis of similarity in polarity, charge, solubility, hydrophobicity, hydrophilicity, and/or the amphipathic nature of the residues, as long as the biological or immunological activity of HELPR is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HELPR which are preferably about 5 to about 15 amino acids in length and which retain some biological activity or immunological activity of HELPR. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp.1–5.)

The term "antagonist," as it is used herein, refers to a molecule which, when bound to HELPR, decreases the amount or the duration of the effect of the biological or immunological activity of HELPR. Antagonists may include proteins, nucleic acids, carbohydrates, antibodies, or any other molecules which decrease the effect of HELPR.

As used herein, the term "antibody" refers to intact molecules as well as to fragments thereof, such as Fa, F(ab')$_2$, and Fv fragments, which are capable of binding the epitopic determinant. Antibodies that bind HELPR polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HELPR, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HELPR or fragments of HELPR may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HELPR, by northern analysis is indicative of the presence of nucleic acids encoding HELPR in a sample, and thereby correlates with expression of the transcript from the polynucleotide encoding HELPR.

A "deletion," as the term is used herein, refers to a change in the amino acid or nucleotide sequence that results in the absence of one or more amino acid residues or nucleotides.

The term "derivative," as used herein, refers to the chemical modification of HELPR, of a polynucleotide sequence encoding HELPR, or of a polynucleotide sequence complementary to a polynucleotide sequence encoding HELPR. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of HELPR. For example, modulation may cause an increase or a decrease in protein activity, binding characteristics, or any other biological, functional, or immunological properties of HELPR.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HELPR, or fragments thereof, or HELPR itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HELPR, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The Invention

The invention is based on the discovery of a new human E1-like protein (HELPR), the polynucleotides encoding HELPR, and the use of these compositions for the diagnosis, treatment, or prevention of cell proliferative, immunological, neurological, and reproductive disorders.

Nucleic acids encoding the HELPR of the present invention were first identified in Incyte Clone 2546462 from the uterine myometrium cDNA library (UTRSNOT11) using a computer search for amino acid sequence alignments. A consensus sequence, SEQ ID NO:2, was derived from the following overlapping and/or extended nucleic acid sequences: Incyte Clones 2546462 (UTRSNOT11), 3768087 (BRSTNOT24), 490621 (HNT2AGT01), 3207877 (PENCNOT03), 495436 (HNT2NOT01), 2654836 (THYMNOT04), 2947271 (BRAITUT23), 2630795 (COLNTUT15), and 127098 (TESTNOT01).

In one embodiment, the invention encompasses a polypeptide comprising the amino acid sequence of SEQ ID NO:1, as shown in FIGS. 1A, 1B, 1C, 1D, and 1E. HELPR is 363 amino acids in length and has a potential N-glycosylation site at $N_{131}$; a potential cAMP- and cGMP-dependent protein kinase phosphorylation site at $S_{342}$; a potential casein kinase II phosphorylation site at $T_{31}$; and three potential protein kinase C phosphorylation sites at $T_{48}$, $T_{277}$, and $S_{343}$. Amino acid sequence analysis using software that surveys the BLOCKS database of conserved protein families indicates, with strong statistical support, that HELPR contains 8 out of 11 highly conserved regions found in E1 ubiquitin-activating enzymes. In addition, the consensus ATP-binding site present in E1 ubiquitin-activating enzymes is conserved in HELPR from $G_{55}$ to $G_{60}$. As shown in FIGS. 2A, 2B, and 2C, HELPR has chemical and structural homology with E1-like proteins. In particular, HELPR shares homology with the CESAB54F cDNA product from the nematode Caenorhabditis elegans (GI 1055197; SEQ ID NO:3) and with Uba2p from the yeast Saccharomyces cerevisiae (GI 793879; SEQ ID NO:4). HELPR and CESAB54F share 48% identity, and HELPR and Uba2p share 24% identity. Note that divergent amino acids in Uba2p from residues 196 to 368 and from residue 382 to the C-terminal residue 636 are not included in FIG. 2B for reasons of clarity. However, these residues are included in the calculation of amino acid identity with HELPR. The E1 active site cysteine residue is also conserved in HELPR at $C_{216}$, as are three adjacent residues of the E1 active site consensus sequence at $P_{214}$, $M_{215}$, and $T_{217}$. The potential phosphorylation site at $T_{48}$ of HELPR is conserved in Uba2p. A region of unique sequence in HELPR from about amino acid 18 to about amino acid 30 is encoded by a fragment of SEQ ID NO:2 from about nucleotide 120 to about nucleotide 158. Northern analysis shows the expression of this sequence in various libraries, at least 66% of which are associated with cell proliferation and at least 26% of which are associated with immune response. In addition, 28% of the libraries expressing HELPR are derived from reproductive tissue, and 21% are derived from neural tissue.

The invention also encompasses HELPR variants. A preferred HELPR variant is one which has at least about 80%, more preferably at least about 90%, and most preferably at least about 95% amino acid sequence identity to the HELPR amino acid sequence, and which contains at least one functional or structural characteristic of HELPR.

The invention also encompasses polynucleotides which encode HELPR. In a particular embodiment, the invention encompasses a polynucleotide sequence comprising the sequence of SEQ ID NO:2, which encodes an HELPR.

The invention also encompasses a variant of a polynucleotide sequence encoding HELPR. In particular, such a variant polynucleotide sequence will have at least about 80%, more preferably at least about 90%, and most preferably at least about 95% polynucleotide sequence identity to the polynucleotide sequence encoding HELPR. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of HELPR.

It will be appreciated by those skilled in the art that as a result of the degeneracy of the genetic code, a multitude of polynucleotide sequences encoding HELPR, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HELPR, and all such variations are to be considered as being specifically disclosed.

Although nucleotide sequences which encode HELPR and its variants are preferably capable of hybridizing to the nucleotide sequence of the naturally occurring HELPR under appropriately selected conditions of stringency, it may be advantageous to produce nucleotide sequences encoding HELPR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HELPR and its derivatives without altering the encoded amino acid sequences include the production of RNA transcripts having more desirable properties, such as a greater half-life, than transcripts produced from the naturally occurring sequence.

The invention also encompasses production of DNA sequences which encode HELPR and HELPR derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HELPR or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System (GIBCO/BRL, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HELPR may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer which is complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HELPR may be used in recombinant DNA molecules to direct expression of HELPR, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HELPR.

As will be understood by those of skill in the art, it may be advantageous to produce HELPR-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HELPR-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HELPR may be ligated to a heterologous sequence to encode a fusion protein. For example, to screen peptide libraries for inhibitors of HELPR activity, it may be useful to encode a chimeric HELPR protein that can be recognized by a commercially available antibody. A fusion protein may also be engineered to contain a cleavage site located between the HELPR encoding sequence and the heterologous protein sequence, so that HELPR may be cleaved and purified away from the heterologous moiety.

In another embodiment, sequences encoding HELPR may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, the protein itself may be produced using chemical methods to synthesize the amino acid sequence of HELPR, or a fragment thereof. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer). Additionally, the amino acid sequence of HELPR, or any part thereof, may be altered during direct synthesis and/or combined with sequences from other proteins, or any part thereof, to produce a variant polypeptide.

The peptide may be substantially purified by preparative high performance liquid chromatography. (See, e.g., Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins Structures and Molecular Properties*, WH Freeman and Co., New York, N.Y.)

In order to express a biologically active HELPR, the nucleotide sequences encoding HELPR or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HELPR and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HELPR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HELPR which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the Bluescript® phagemid (Stratagene, La Jolla, Calif.) or pSport1™ plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HELPR, vectors based on SV40 or EBV may be used with an appropriate selectable marker.

In bacterial systems, a number of expression vectors may be selected depending upon the use intended for HELPR. For example, when large quantities of HELPR are needed for the induction of antibodies, vectors which direct high level expression of fusion proteins that are readily purified may be used. Such vectors include, but are not limited to, multifunctional *E. coli* cloning and expression vectors such as Bluescript® (Stratagene), in which the sequence encoding HELPR may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Amersham Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HELPR may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HELPR. For example, in one such system, *Autographa californica* nuclear polyhedrosis virus (AcNPV) is used as a vector to express foreign genes in *Spodoptera frugiperda* cells or in Trichoplusia larvae. The sequences encoding HELPR may be cloned into a non-essential region of the virus, such as the polyhedrin gene, and placed under control of the polyhedrin promoter. Successful insertion of sequences encoding HELPR will render the polyhedrin gene inactive and produce recombinant virus lacking coat protein. The recombinant viruses may then be used to infect, for example, *S. frugiperda* cells or Trichoplusia larvae in which HELPR may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HELPR may be ligated into an adenovirus transcription/translation complex consisting of the late promoter and tripartite leader sequence. Insertion in a non-essential E1 or E3 region of the viral genome may be used to obtain a viable virus which is capable of expressing HELPR in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HELPR. Such signals include the ATG initiation codon and adjacent sequences. In cases where sequences encoding HELPR and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HELPR can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in $tk^-$ or $apr^-$ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, β glucuronidase and its substrate GUS, luciferase and its substrate luciferin may be used. Green fluorescent proteins (GFP) (Clontech, Palo Alto, Calif.) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HELPR is inserted within a marker gene sequence, transformed cells containing sequences encoding HELPR can be identified by the absence of marker gene function. Alternatively, a marker gene can be placed in tandem with a sequence encoding HELPR under the control of a single promoter. Expression of the marker gene in response to induction or selection usually indicates expression of the tandem gene as well.

Alternatively, host cells which contain the nucleic acid sequence encoding HELPR and express HELPR may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HELPR can be detected by DNA-DNA or DNA-RNA hybridization or amplification using probes or fragments or fragments of polynucleotides encoding HELPR. Nucleic acid amplification based assays involve the use of oligonucleotides or oligomers based on the sequences encoding HELPR to detect transformants containing DNA or RNA encoding HELPR.

A variety of protocols for detecting and measuring the expression of HELPR, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HELPR is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HELPR include oligolabeling, nick translation, end-labeling, or PCR amplification using a labeled nucleotide. Alternatively, the sequences encoding HELPR, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HELPR may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HELPR may be designed to contain signal sequences which direct secretion of HELPR through a prokaryotic or eukaryotic cell membrane. Other constructions may be used to join sequences encoding HELPR to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HELPR encoding sequence may be used to facilitate purification. One such expression vector provides for expression of a fusion protein containing HELPR and a nucleic acid encoding 6 histidine residues preceding a thioredoxin or an enterokinase cleavage site. The histidine residues facilitate purification on immobilized metal ion affinity chromatography (IMAC). (See, e.g., Porath, J. et al. (1992) Prot. Exp. Purif. 3: 263–281.) The enterokinase cleavage site provides a means for purifying HELPR from the fusion protein. (See, e.g., Kroll, D. J. et al. (1993) DNA Cell Biol. 12:441–453.)

Fragments of HELPR may be produced not only by recombinant production, but also by direct peptide synthesis using solid-phase techniques. (See, e.g., Creighton, T. E. (1984) Protein: Structures and Molecular Properties, pp. 55–60, W.H. Freeman and Co., New York, N.Y.) Protein synthesis may be performed by manual techniques or by automation. Automated synthesis may be achieved, for example, using the Applied Biosystems 431A Peptide Synthesizer (Perkin Elmer). Various fragments of HELPR may be synthesized separately and then combined to produce the full length molecule.

Therapeutics

Chemical and structural homology exists among HELPR, CESAB54F from nematode (GI 1055197) and Uba2p from yeast (GI 793879). In addition, HELPR is expressed in neural and reproductive tissues. Therefore, HELPR appears to play a role in cell proliferative, immunological, neurological, and reproductive disorders.

Therefore, in one embodiment, an antagonist of HELPR may be administered to a subject to treat or prevent a cell proliferative disorder. Such disorders may include, but are not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HELPR may be used directly as an antagonist or indirectly as a targeting or delivery mechanism for bringing a pharmaceutical agent to cells or tissue which express HELPR.

In an additional embodiment, a vector expressing the complement of the polynucleotide encoding HELPR may be administered to a subject to treat or prevent a cell proliferative disorder including, but not limited to, those described above.

In another embodiment, HELPR or a fragment or derivative thereof may be administered to a subject to treat or prevent an immunological disorder. Such disorders can include, but are not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; trauma, X-linked agammaglobinemia of Bruton, common variable immunodeficiency (CVI), DiGeorge's syndrome (thymic hypoplasia), isolated IgA deficiency, severe combined immunodeficiency diseases (SCID), and immunodeficiency with thrombocytopenia and eczema (Wiskott-Aldrich syndrome).

In another embodiment, a vector capable of expressing HELPR or a fragment or derivative thereof may be administered to a subject to treat or prevent an immunological disorder including, but not limited to, those described above.

In a further embodiment, a pharmaceutical composition comprising a substantially purified HELPR in conjunction with a suitable pharmaceutical carrier may be administered to a subject to treat or prevent an immunological disorder including, but not limited to, those provided above.

In still another embodiment, an agonist which modulates the activity of HELPR may be administered to a subject to treat or prevent an immunological disorder including, but not limited to, those listed above.

In a further embodiment, an antagonist of HELPR may be administered to a subject to treat or prevent an immunological disorder. Such disorders may include, but are not limited to, those discussed above. In one aspect, an antibody which specifically binds HELPR may be used directly as an antagonist or indirectly as a targeting or delivery mechanism for bringing a pharmaceutical agent to cells or tissue which express HELPR.

In an additional embodiment, a vector expressing the complement of the polynucleotide encoding HELPR may be administered to a subject to treat or prevent a an immunological disorder including, but not limited to, those described above.

In another embodiment, an antagonist of HELPR may be administered to a subject to treat or prevent a neurological disorder. Such disorders may include, but are not limited to, akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder. In one aspect, an antibody which specifically binds HELPR may be used directly as an antagonist or indirectly as a targeting or delivery mechanism for bringing a pharmaceutical agent to cells or tissue which express HELPR.

In an additional embodiment, a vector expressing the complement of the polynucleotide encoding HELPR may be administered to a subject to treat or prevent a neurological disorder including, but not limited to, those described above.

In another embodiment, HELPR or a fragment or derivative thereof may be administered to a subject to treat or prevent a reproductive disorder. Such disorders can include, but are not limited to, abnormal prolactin production, infertility, tubal disease, ovulatory defects, endometriosis, perturbations of the estrous and menstrual cycles, polycystic ovary syndrome, ovarian hyperstimulation syndrome, endometrial and ovarian tumors, autoimmune disorders, ectopic pregnancy, teratogenesis, breast cancer, fibrocystic breast disease, galactorrhea, abnormal spermatogenesis, abnormal sperm physiology, testicular cancer, prostate cancer, benign prostatic hyperplasia, prostatitis, and gynecomastia.

In another embodiment, a vector capable of expressing HELPR or a fragment or derivative thereof may be administered to a subject to treat or prevent a reproductive disorder including, but not limited to, those described above.

In a further embodiment, a pharmaceutical composition comprising a substantially purified HELPR in conjunction with a suitable pharmaceutical carrier may be administered to a subject to treat or prevent a reproductive disorder including, but not limited to, those provided above.

In still another embodiment, an agonist which modulates the activity of HELPR may be administered to a subject to treat or prevent a reproductive disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HELPR may be produced using methods which are generally known in the art. In particular, purified HELPR may be used to produce antibodies or to screen libraries of pharmaceutical agents to identify those which specifically bind HELPR. Antibodies to HELPR may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HELPR or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HELPR have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HELPR amino acids may be fused with those of another protein, such as KLH, and antibodies to the chimeric molecule may be produced.

Monoclonal antibodies to HELPR may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc.

Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HELPR-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HELPR may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HELPR and its specific antibody. A two-site, monoclonal-based immunoassay utilizing monoclonal antibodies reactive to two non-interfering HELPR epitopes is preferred, but a competitive binding assay may also be employed. (Maddox, supra.)

In another embodiment of the invention, the polynucleotides encoding HELPR, or any fragment or complement thereof, may be used for therapeutic purposes. In one aspect, the complement of the polynucleotide encoding HELPR may be used in situations in which it would be desirable to block the transcription of the mRNA. In particular, cells may be transformed with sequences complementary to polynucleotides encoding HELPR. Thus, complementary molecules or fragments may be used to modulate HELPR activity, or to achieve regulation of gene function. Such technology is now well known in the art, and sense or antisense oligonucleotides or larger fragments can be designed from various locations along the coding or control regions of sequences encoding HELPR.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HELPR. (See, e.g., Sambrook, supra; and Ausubel, supra.)

Genes encoding HELPR can be turned off by transforming a cell or tissue with expression vectors which express high levels of a polynucleotide, or fragment thereof, encoding HELPR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HELPR. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HELPR.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HELPR. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HELPR, antibodies to HELPR, and mimetics, agonists, antagonists, or inhibitors of HELPR. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HELPR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HELPR or fragments thereof, antibodies of HELPR, and agonists, antagonists or inhibitors of HELPR, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD50$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HELPR may be used for the diagnosis of disorders characterized by expression of HELPR, or in assays to monitor patients being treated with HELPR or agonists, antagonists, or inhibitors of HELPR. Antibodies useful for diagnostic purposes may be prepared in the same manner as described above for therapeutics. Diagnostic assays for HELPR include methods which utilize the antibody and a label to detect HELPR in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HELPR, including ELISAs, RIAs, and FACS, are known in the art and provide a basis for diagnosing altered or abnormal levels of HELPR expression. Normal or standard values for HELPR expression are established by combining body fluids or cell extracts taken from normal mammalian subjects, preferably human, with antibody to HELPR under conditions suitable for complex formation The amount of standard complex formation may be quantitated by various methods, preferably by photometric means. Quantities of HELPR expressed in subject, control, and disease samples from biopsied tissues are compared with the standard values. Deviation between standard and subject values establishes the parameters for diagnosing disease.

In another embodiment of the invention, the polynucleotides encoding HELPR may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HELPR may be correlated with disease. The diagnostic assay may be used to determine absence, presence, and excess expression of HELPR, and to monitor regulation of HELPR levels during therapeutic intervention.

In one aspect, hybridization with PCR probes which are capable of detecting polynucleotide sequences, including genomic sequences, encoding HELPR or closely related molecules may be used to identify nucleic acid sequences which encode HELPR. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HELPR, alleles, or related sequences.

Probes may also be used for the detection of related sequences, and should preferably have at least 50% sequence identity to any of the HELPR encoding sequences. The hybridization probes of the subject invention may be DNA or RNA and may be derived from the sequence of SEQ ID NO:2 or from genomic sequences including promoters, enhancers, and introns of the HELPR gene.

Means for producing specific hybridization probes for DNAs encoding HELPR include the cloning of polynucleotide sequences encoding HELPR or HELPR derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HELPR may be used for the diagnosis of a disorder associated with expression of HELPR. Examples of such a disorder include, but are not limited to, a cell proliferative disorder such as arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an immunological disorder such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; trauma, X-linked agammaglobinemia of Bruton, common variable immunodeficiency (CVI), DiGeorge's syndrome (thymic hypoplasia), isolated IgA deficiency, severe combined immunodeficiency diseases (SCID), and immunodeficiency with thrombocytopenia and eczema (Wiskott-Aldrich syndrome); a neurological disorder such as akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder; and a reproductive disorder such as abnormal prolactin production, infertility, tubal disease, ovulatory defects, endometriosis, perturbations of the estrous and menstrual cycles, polycystic ovary syndrome, ovarian hyperstimulation syndrome, endometrial and ovarian tumors, autoimmune disorders, ectopic pregnancy, teratogenesis, breast cancer, fibrocystic breast disease, galactorrhea, abnormal spermatogenesis, abnormal sperm physiology, testicular cancer, prostate cancer, benign prostatic hyperplasia, prostatitis, and gynecomastia. The polynucleotide sequences encoding HELPR may be used in Southern or northern analysis, dot blot, or other membrane-based technologies; in PCR technologies; in dipstick, pin, and ELISA assays; and in microarrays utilizing fluids or tissues from patients to detect altered HELPR expression. Such qualitative or quantitative methods are well known in the art.

In a particular aspect, the nucleotide sequences encoding HELPR may be useful in assays that detect the presence of associated disorders, particularly those mentioned above. The nucleotide sequences encoding HELPR may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HELPR in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HELPR, a normal or standard profile for expression is established. This may be accomplished by combining body fluids or cell extracts taken from normal subjects, either animal or human, with a sequence, or a fragment thereof, encoding HELPR, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HELPR may involve the use of PCR. These oligomers may be chemically synthesized, generated enzymatically, or produced in vitro. Oligomers will preferably contain a fragment of a polynucleotide encoding HELPR, or a fragment of a polynucleotide complementary to the polynucleotide encoding HELPR, and will be employed under optimized conditions for identification of a specific gene or condition. Oligomers may also be employed under less stringent conditions for detection or quantitation of closely related DNA or RNA sequences.

Methods which may also be used to quantitate the expression of HELPR include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HELPR may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HELPR on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HELPR, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HELPR and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HELPR, or fragments thereof, and washed. Bound HELPR is then detected by methods well known in the art. Purified HELPR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HELPR specifically compete with a test compound for binding HELPR. In this manner, antibodies can be used to detect the presence of any peptide which shares one or more antigenic determinants with HELPR.

In additional embodiments, the nucleotide sequences which encode HELPR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. UTRSNOT11 cDNA Library Construction

The UTRSNOT11 cDNA library was constructed from uterine myometrial tissue obtained from a 43-year-old female during vaginal hysterectomy and removal of the fallopian tubes and ovaries. Pathology indicated that the uterine myometrium contained an intramural and a submucosal leiomyoma. Family history included malignant colon neoplasms in the mother, father, and grandparent.

The frozen tissue was homogenized and lysed in TRIzol reagent (1 gm tissue/10 ml TRIzol; Catalog #10296-028, Gibco/BRL, Gaithersburg, Md.), a monoplastic solution of phenol and guanidine isothiocyanate, using a Brinkmann Homogenizer Polytron PT-3000 (Brinkmann Instruments, Westbury, N.Y.). After brief incubation on ice, chloroform was added (1:5 v/v), and the mixture was centrifuged to separate the phases. The upper aqueous phase was removed to a fresh tube, and isopropanol was added to precipitate RNA. The RNA was resuspended in RNase-free water and treated with DNase. The RNA was re-extracted three times with acid phenol-chloroform and reprecipitated with sodium acetate and ethanol. Poly(A+) RNA was isolated using the Qiagen Oligotex kit (QIAGEN, Chatsworth, Calif.).

Poly (A+) RNA was used to construct the UTRSNOT11 cDNA library according to the recommended protocols in the SuperScript Plasmid System (Catalog #18248-013, Gibco/BRL). The cDNAs were fractionated on a Sepharose CL4B column (Catalog #275105-01, Pharmacia, Piscataway, N.J.), and those cDNAs exceeding 400 bp were ligated into the plasmid pINCY 1 (Incyte). pINCY 1 was subsequently transformed into DH5α™ competent cells (Catalog #18258-012, Gibco/BRL).

II. Isolation and Sequencing of cDNA Clones

Plasmid DNA was released from the cells and purified using the REAL Prep 96 plasmid kit (Catalog #26173, QIAGEN). The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after the cultures were incubated for 19 hours, the cells were lysed with 0.3 ml of lysis buffer; and 3) following isopropanol precipitation, the plasmid DNA pellets were each resuspended in 0.1 ml of distilled water. The DNA samples were stored at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III. Homology Searching of cDNA Clones and their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HELPR occurs. Abundance and percent abundance are also reported. Abundance directly reflects the number of times a particular transcript is represented in a cDNA library, and percent abundance is abundance divided by the total number of sequences examined in the cDNA library.

V. Extension of HELPR Encoding Polynucleotides

The nucleic acid sequence of Incyte Clone 2546462 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |

-continued

| Step 8  | 94° C. for 15 sec |
| Step 9  | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2×carb). The following day, several colonies were randomly picked from each plate and cultured in 150 µl of liquid LB/2×Carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 µCi of [$\gamma$-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HELPR-encoding sequences, or any parts thereof, are used to detect, decrease, or inhibit expression of naturally occurring HELPR. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HELPR. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HELPR-encoding transcript.

IX. Expression of HELPR

Expression of HELPR is accomplished by subcloning the cDNA into an appropriate vector and transforming the vector into host cells. This vector contains an appropriate promoter, e.g., β-galactosidase, upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HELPR into bacterial growth media which can be used directly in the following assay for activity.

X. Demonstration of HELPR Activity

HELPR activity is demonstrated by its ability to form a covalent thiolester bond with ubiquitin (Ub). This activity can be detected and quantified using a "covalent affinity" chromatography procedure. (Ciechanover, A. et al. (1982) J. Biol. Chem. 257:2537–2542.) Ub is first conjugated to Sepharose, an inert resin, using methods well known by those skilled in the art. HELPR, produced by recombinant methods or purified biochemically, is present in a solution containing ATP and magnesium ions. This solution is exposed to the Ub-Sepharose conjugate in a column chromatography format. Ub-Sepharose is washed with a solution containing a high concentration of salt, such as sodium chloride. This treatment is effective in removing virtually all proteins that are not covalently bound to Ub-Sepharose. HELPR covalently bound to Ub-Sepharose is eluted with a thiol compound such as dithiothreitol. The presence of HELPR in the eluent is detected by SDS-polyacrylamide gel electrophoresis and gel staining. Immunological methods such as western blot which utilize specific antibody directed against HELPR are used to quantify the amount of HELPR in the eluent. The amount of HELPR that binds to Ub-Sepharose is proportional to the activity of HELPR.

XI. Production of HELPR Specific Antibodies

HELPR substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the HELPR amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HELPR Using Specific Antibodies

Naturally occurring or recombinant HELPR is substantially purified by immunoaffinity chromatography using antibodies specific for HELPR. An immunoaffinity column is constructed by covalently coupling anti-HELPR antibody to an activated chromatographic resin, such as CNBr-activated Sepharose (Pharmacia & Upjohn). After the coupling, the resin is blocked and washed according to the manufacturer's instructions.

Media containing HELPR are passed over the immunoaffinity column, and the column is washed under conditions that allow the preferential absorbance of HELPR (e.g., high ionic strength buffers in the presence of detergent). The column is eluted under conditions that disrupt antibody/HELPR binding (e.g., a buffer of pH 2 to pH 3, or a high concentration of a chaotrope, such as urea or thiocyanate ion), and HELPR is collected.

XIII. Identification of Molecules Which Interact with HELPR

HELPR, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HELPR, washed, and any wells with labeled HELPR complex are assayed. Data obtained using different concentrations of HELPR are used to calculate values for the number, affinity, and association of HELPR with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 363 amino acids

```
            (B) TYPE: amino acid
            (C) STRANDEDNESS: single
            (D) TOPOLOGY: linear (vii) IMMEDIATE SOURCE:
            (A) LIBRARY: UTRSNOT11
            (B) CLONE: 2546462

(xi) SEQUENCE DESCRIPTION: SEQ ID NO:1:

Met Ala Val Asp Gly Gly Cys Gly Asp Thr Gly Asp Trp Glu Gly Arg
 1               5                  10                  15

Trp Asn His Val Lys Lys Phe Leu Glu Arg Ser Gly Pro Phe Thr His
                20                  25                  30

Pro Asp Phe Glu Pro Ser Thr Glu Ser Leu Gln Phe Leu Leu Asp Thr
            35                  40                  45

Cys Lys Val Leu Val Ile Gly Ala Gly Gly Leu Gly Cys Glu Leu Leu
 50                  55                  60

Lys Asn Leu Ala Leu Ser Gly Phe Arg Gln Ile His Val Ile Asp Met
65                  70                  75                  80

Asp Thr Ile Asp Val Ser Asn Leu Asn Arg Gln Phe Leu Phe Arg Pro
                85                  90                  95

Lys Asp Ile Gly Arg Pro Lys Ala Glu Val Ala Ala Glu Phe Leu Asn
            100                 105                 110

Asp Arg Val Pro Asn Cys Asn Val Val Pro His Phe Asn Lys Ile Gln
            115                 120                 125

Asp Phe Asn Asp Thr Phe Tyr Arg Gln Phe His Ile Ile Val Cys Gly
            130                 135                 140

Leu Asp Ser Ile Ile Ala Arg Arg Trp Ile Asn Gly Met Leu Ile Ser
145                 150                 155                 160

Leu Leu Asn Tyr Glu Asp Gly Val Leu Asp Pro Ser Ser Ile Val Pro
                165                 170                 175

Leu Ile Asp Gly Gly Thr Glu Gly Phe Lys Gly Asn Ala Arg Val Ile
            180                 185                 190

Leu Pro Gly Met Thr Ala Cys Ile Glu Cys Thr Leu Glu Leu Tyr Pro
            195                 200                 205

Pro Gln Val Asn Phe Pro Met Cys Thr Ile Ala Ser Met Pro Arg Leu
            210                 215                 220

Pro Glu His Cys Ile Glu Tyr Val Arg Met Leu Gln Trp Pro Lys Glu
225                 230                 235                 240

Gln Pro Phe Gly Glu Gly Val Pro Leu Asp Gly Asp Pro Glu His
                245                 250                 255

Ile Gln Trp Ile Phe Gln Lys Ser Leu Glu Arg Ala Ser Gln Tyr Asn
            260                 265                 270

Ile Arg Gly Val Thr Tyr Arg Leu Thr Gln Gly Val Val Lys Arg Ile
            275                 280                 285

Ile Pro Ala Val Ala Ser Thr Asn Ala Val Ile Ala Ala Val Cys Ala
            290                 295                 300

Thr Glu Val Phe Lys Ile Ala Thr Ser Ala Tyr Ile Pro Leu Asn Asn
305                 310                 315                 320

Tyr Leu Val Phe Asn Asp Val Asp Gly Leu Tyr Thr Tyr Thr Phe Glu
                325                 330                 335

Ala Glu Arg Lys Val Ser Ser Ile Lys Asn Thr Phe Leu Ile Met His
            340                 345                 350

Ile Leu Ile Phe Lys Tyr Tyr Trp Leu Glu Ile
            355                 360
```

(2) INFORMATION FOR SEQ ID NO:2:

(i) SEQUENCE CHARACTERISTICS:
  (A) LENGTH: 2084 base pairs
  (B) TYPE: nucleic acid
  (C) STRANDEDNESS: single
  (D) TOPOLOGY: linear (vii) IMMEDIATE SOURCE:
  (A) LIBRARY: UTRSNOT11
  (B) CLONE: 2546462

(xi) SEQUENCE DESCRIPTION: SEQ ID NO:2:

```
AACAATATGG CGGATGGCGA GGAGCGGAGA AGAAAAGAAG GAGAATAGAG GAGCTGCTGG      60

CTGAGAAAAT GGCTGTTGAT GGTGGGTGTG GGGACACTGG AGACTGGGAA GGTCGCTGGA     120

ACCATGTAAA GAAGTTCCTC GAGCGATCTG GACCCTTCAC ACACCCTGAT TTCGAACCGA     180

GCACTGAATC TCTCCAGTTC TTGTTAGATA CATGTAAAGT TCTAGTCATT GGAGCTGGCG     240

GCTTAGGATG TGAGCTCCTG AAAAATCTGG CCTTGTCTGG TTTTAGACAG ATTCATGTTA     300

TAGATATGGA CACTATAGAT GTTTCCAATC TAAATAGGCA GTTTTATTT AGGCCTAAAG      360

ATATTGGAAG ACCTAAGGCT GAAGTTGCTG CAGAATTTCT AAATGACAGA GTTCCTAATT     420

GCAATGTAGT TCCACATTTC AACAAGATTC AAGATTTTAA CGACACTTTC TATCGACAAT     480

TTCATATTAT TGTATGTGGA CTGGACTCTA TCATCGCCAG AAGATGGATA AATGGCATGC     540

TGATATCTCT TCTAAATTAT GAAGATGGTG TCTTAGATCC AAGCTCCATT GTCCCTTTGA     600

TAGACGGGGG GACAGAAGGT TTTAAAGGAA ATGCCCGGGT GATTCTGCCT GGAATGACTG     660

CTTGTATCGA ATGCACGCTG GAACTTTATC CACCACAGGT TAATTTTCCC ATGTGCACCA     720

TTGCATCTAT GCCCAGGCTA CCAGAACACT GTATTGAGTA TGTAAGGATG TTGCAGTGGC     780

CTAAGGAGCA GCCTTTTGGA GAAGGGGTTC CATTAGATGG AGATGATCCT GAACATATAC     840

AATGGATTTT CCAAAAATCC CTAGAGAGAG CATCACAATA TAATATTAGG GGTGTTACGT     900

ATAGGCTCAC TCAAGGGGTA GTAAAAAGAA TCATTCCTGC AGTAGCTTCC ACAAATGCAG     960

TCATTGCAGC TGTGTGTGCC ACTGAGGTTT TTAAAATAGC CACAAGTGCA TACATTCCCT    1020

TGAATAATTA CTTGGTGTTT AATGATGTAG ATGGGCTGTA TACATACACA TTTGAAGCAG    1080

AAAGAAAGGT TAGTAGTATT AAGAACACAT TTTTGATCAT GCATATTTTG ATTTTTAAAT    1140

ATTATTGGTT AGAAATTTGA ACAAAGTCAC CCATACATTT TCTAACTTCC AGAACTCTAC    1200

TTATTATATA TCTTTTGCTT TATAGCCTGA ATAACTCTA TAGCGAAGTA ATTTACAAGA     1260

AATGGTCTAT TATGAAAAGC AGGCTTTAAA GCATAAAAAT TTTTTTATAG GAAATATGCA    1320

TGATTATAAA ACAACCTGAT TTTTATTTTA TTGTTCATAA AAGAGACTAA TATTGGTGCA    1380

TGTGCTGCTG TAATTTGTTG TGTATTATGT GTGTAGGAAA ACTGCCCAGC TTGTAGCCAG    1440

CTTCCTCAAA ATATTCAGTT TTCTCCATCA GCTAAACTAC AGGAGGTTTT GGATTATCTA    1500

ACCAATAGTG CTTCTCTGTA AGTATTGTAG ATTTTTGTTA TGTTGTAAAA ATCATTTTTG    1560

TGATTTTTGA AACCTTAAAA AAATTATCTT TTGATAAAAA TTATGTTTGA TACTTCTCTC    1620

TCATCATAAT CTTTAGGCAA ATGAAATCTC CAGCCATCAC AGCCACCCTA GAGGGAAAAA    1680

ATAGAACACT TTACTTACAG GTTATCAATG TGTATTTTAA ATTTTTTTCA GAAAATTATA    1740

TCAAGTTTTA TTTTACTTTA ATGTGTCTTA CATTAAAGTA ATTTTGTTTT CTAGTCGGTA    1800

ACCTCTATTG AAGAACGAAC AAGGCCAAAT CTCTCCAAAA CATTGAAAGG TATTTTACAT    1860

AAGGGTATTT ACTAATCATT TTCTTTCTTT TCTCTCTTTT TGGTGAAAGT AATCAGTGCT    1920
```

| TGTTCTAGAT TTCCTCTTAA TGCCTTGTAT ATGGTCAGGT AATAATTACT TACAACTTTA | 1980 |
| GACATATTAA TAGAATTAAT TGCTCTTTTA GTAGGATATT TAAAATCTCC AAGGAATCAA | 2040 |
| TATTTACTTT GATTAAAGAG GATTGGNTTT TGATGTTTTN CTAG | 2084 |

(2) INFORMATION FOR SEQ ID NO:3:

(i) SEQUENCE CHARACTERISTICS:
        (A) LENGTH: 437 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1055197

(xi) SEQUENCE DESCRIPTION: SEQ ID NO:3:

```
Met Val Ser Val Asp Pro Leu Ala Thr Glu Arg Trp Arg Ser Ile Arg
  1               5                  10                  15

Arg Leu Thr Asp Arg Asp Ser Ala Tyr Lys Val Pro Trp Phe Val Pro
                 20                  25                  30

Gly Pro Glu Asn Phe Glu Ala Leu Gln Asn Thr Lys Ile Leu Val Ile
             35                  40                  45

Gly Ala Gly Gly Leu Gly Cys Glu Leu Leu Lys Asn Leu Ala Leu Ser
 50                  55                  60

Gly Phe Arg Thr Ile Glu Val Ile Asp Met Asp Thr Ile Asp Val Ser
 65                  70                  75                  80

Asn Leu Asn Arg Gln Phe Leu Phe Arg Glu Ser Asp Val Gly Lys Ser
                 85                  90                  95

Lys Ala Glu Val Ala Ala Ala Phe Val Gln Gln Arg Val Val Gly Cys
            100                 105                 110

Gln Asn Tyr Phe Asn Phe Ile Ser Ile Phe Arg His Asn Cys Arg Ile
            115                 120                 125

Glu Asp Lys Gly Gln Glu Phe Tyr Arg Lys Phe Ser Ile Ile Ile Cys
130                 135                 140

Gly Leu Asp Ser Ile Pro Ala Arg Arg Trp Ile Asn Gly Met Leu Cys
145                 150                 155                 160

Asp Leu Val Leu Glu Met Ala Asp Gly Lys Pro Asp Glu Asn Thr Ile
                165                 170                 175

Ile Pro Met Ile Asp Gly Gly Thr Glu Gly Phe Lys Gly Asn Ala Arg
            180                 185                 190

Val Ile Tyr Pro Lys Phe Thr Ala Cys Ile Asp Cys Thr Leu Asp Leu
            195                 200                 205

Tyr Pro Pro Gln Val Asn Phe Pro Leu Cys Thr Ile Ala His Thr Pro
            210                 215                 220

Arg Leu Pro Glu His Cys Ile Glu Tyr Ile Lys Val Val Trp Pro
225                 230                 235                 240

Glu Glu Lys Pro Phe Glu Gly Val Ser Leu Asp Ala Asp Pro Ile
                245                 250                 255

His Val Glu Trp Val Leu Glu Arg Ala Ser Leu Arg Ala Glu Lys Tyr
            260                 265                 270

Asn Ile Arg Gly Val Asp Arg Arg Leu Thr Ser Gly Val Leu Lys Arg
            275                 280                 285

Ile Ile Pro Ala Val Ala Ser Thr Asn Ala Val Ile Ala Ala Ser Cys
            290                 295                 300

Ala Leu Glu Ala Leu Lys Leu Ala Thr Asn Ile Ala Lys Pro Ile Asp
305                 310                 315                 320
```

-continued

```
Asn Tyr Leu Asn Phe Thr Gln Ile His Gly Ala Tyr Thr Ser Val Val
            325                 330                 335

Ser Met Met Lys Asp Asp Asn Cys Leu Thr Cys Ser Gly Gly Arg Leu
            340                 345                 350

Pro Phe Glu Val Ser Pro Ser Ser Thr Leu Glu Ser Leu Ile Ile Arg
            355                 360                 365

Leu Ser Glu Arg Phe His Leu Lys His Pro Thr Leu Ala Thr Ser Thr
            370                 375                 380

Arg Lys Leu Tyr Cys Ile Ser Ser Phe Met Pro Gln Phe Glu Gln Glu
385                 390                 395                 400

Ser Lys Glu Asn Leu His Thr Ser Met Lys Asp Leu Val Ser Asp Gly
            405                 410                 415

Glu Glu Ile Leu Val Ser Asp Glu Ala Leu Ser Arg Ala Leu Thr Leu
            420                 425                 430

Arg Ile Gln Leu Ile
            435
```

(2) INFORMATION FOR SEQ ID NO:4:

(i) SEQUENCE CHARACTERISTICS:
        (A) LENGTH: 636 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 793879

(xi) SEQUENCE DESCRIPTION: SEQ ID NO:4:

```
Met Pro Arg Glu Thr Ser Leu Val Thr Ile Ile Gly Glu Asp Ser Tyr
1               5                   10                  15

Lys Lys Leu Arg Ser Ser Arg Cys Leu Val Gly Ala Gly Gly Ile
            20                  25                  30

Gly Ser Glu Leu Leu Lys Asp Ile Ile Leu Met Glu Phe Gly Glu Ile
            35                  40                  45

His Ile Val Asp Leu Asp Thr Ile Asp Leu Ser Asn Leu Asn Arg Gln
        50                  55                  60

Phe Leu Phe Arg Gln Lys Asp Ile Lys Gln Pro Lys Ser Thr Thr Ala
65                  70                  75                  80

Val Lys Ala Val Gln His Phe Asn Asn Ser Lys Leu Val Pro Tyr Gln
            85                  90                  95

Gly Asn Val Met Asp Ile Ser Thr Phe Pro Leu His Trp Phe Glu Gln
            100                 105                 110

Phe Asp Ile Ile Phe Asn Ala Leu Asp Asn Leu Ala Ala Arg Arg Tyr
            115                 120                 125

Val Asn Lys Ile Ser Gln Phe Leu Ser Leu Pro Leu Ile Glu Ser Gly
            130                 135                 140

Thr Ala Gly Phe Asp Gly Tyr Met Gln Pro Ile Ile Pro Gly Lys Thr
145                 150                 155                 160

Glu Cys Phe Glu Cys Thr Lys Lys Glu Thr Pro Lys Thr Phe Pro Val
            165                 170                 175

Cys Thr Ile Arg Ser Thr Pro Ser Gln Pro Ile His Cys Ile Val Trp
            180                 185                 190

Ala Lys Asn Phe Leu Phe Asn Gln Leu Phe Ala Ser Glu Thr Ser Gly
            195                 200                 205
```

```
Asn Glu Asp Asp Asn Asn Gln Asp Trp Gly Thr Asp Asp Ala Glu Glu
    210                 215                 220
Ile Lys Arg Ile Lys Gln Glu Thr Asn Glu Leu Tyr Glu Leu Gln Lys
225                 230                 235                 240
Ile Ile Ile Ser Arg Asp Ala Ser Arg Ile Pro Glu Ile Leu Asn Lys
                245                 250                 255
Leu Phe Ile Gln Asp Ile Asn Lys Leu Leu Ala Ile Glu Asn Leu Trp
            260                 265                 270
Lys Thr Arg Thr Lys Pro Val Pro Leu Ser Asp Ser Gln Ile Asn Thr
        275                 280                 285
Pro Thr Lys Thr Ala Gln Ser Ala Ser Asn Ser Val Gly Thr Ile Gln
    290                 295                 300
Glu Gln Ile Ser Asn Phe Ile Asn Ile Thr Gln Lys Leu Met Asp Arg
305                 310                 315                 320
Tyr Pro Lys Glu Gln Asn His Ile Glu Phe Asp Lys Asp Asp Ala Asp
                325                 330                 335
Thr Leu Glu Phe Val Ala Thr Ala Ala Asn Ile Arg Ser His Ile Phe
            340                 345                 350
Asn Ile Pro Met Lys Ser Val Phe Asp Ile Lys Gln Ile Ala Gly Asn
        355                 360                 365
Ile Ile Pro Ala Ile Ala Thr Thr Asn Ala Ile Val Ala Gly Ala Ser
    370                 375                 380
Ser Leu Ile Ser Leu Arg Val Leu Asn Leu Leu Lys Tyr Ala Pro Thr
385                 390                 395                 400
Thr Lys Tyr Thr Asp Leu Asn Met Ala Phe Thr Ala Lys Ala Ser Asn
                405                 410                 415
Leu Ser Gln Asn Arg Tyr Leu Ser Asn Pro Lys Leu Ala Pro Pro Asn
            420                 425                 430
Lys Asn Cys Pro Val Cys Ser Lys Val Cys Arg Gly Val Ile Lys Leu
        435                 440                 445
Ser Ser Asp Cys Leu Asn Lys Met Lys Leu Ser Asp Phe Val Val Leu
    450                 455                 460
Ile Arg Glu Lys Tyr Ser Tyr Pro Gln Asp Ile Ser Leu Leu Asp Ala
465                 470                 475                 480
Ser Asn Gln Arg Leu Leu Phe Asp Tyr Asp Phe Glu Asp Leu Asn Asp
                485                 490                 495
Arg Thr Leu Ser Glu Ile Asn Leu Gly Asn Gly Ser Ile Ile Leu Phe
            500                 505                 510
Ser Asp Glu Glu Gly Asp Thr Met Ile Arg Lys Ala Ile Glu Leu Phe
        515                 520                 525
Leu Asp Val Asp Asp Glu Leu Pro Cys Asn Thr Cys Ser Leu Pro Asp
    530                 535                 540
Val Glu Val Pro Leu Ile Lys Ala Asn Asn Ser Pro Ser Lys Asn Glu
545                 550                 555                 560
Glu Glu Glu Lys Asn Glu Lys Gly Ala Asp Val Val Ala Thr Thr Asn
                565                 570                 575
Ser His Gly Lys Asp Gly Ile Val Ile Leu Asp Asp Glu Gly Glu
            580                 585                 590
Ile Thr Ile Asp Ala Glu Pro Ile Asn Gly Ser Lys Lys Arg Pro Val
        595                 600                 605
Asp Thr Glu Ile Ser Glu Ala Pro Ser Asn Lys Arg Thr Lys Leu Val
    610                 615                 620
```

```
-continued

Asn Glu Pro Thr Asn Ser Asp Ile Val Glu Leu Asp
625                 630             635
```

What is claimed is:

1. An isolated and purified polynucleotide comprising the polynucleotide sequence of SEQ ID NO:2.

2. An isolated polynucleotide encoding a polypeptide selected from the group consisting of:
   (i) a polypeptide comprising the amino acid sequence of SEQ ID NO:1; and
   (ii) a naturally-occurring polypeptide having at least 90% sequence identity to the sequence of SEQ ID NO:1, wherein said polypeptide activates ubiquitin.

3. An isolated polynucleotide encoding a polypeptide, said polypeptide comprising an amino acid sequence as shown in SEQ ID NO:1, wherein said polypeptide activates ubiquitin.

4. An isolated polynucleotide of claim 3, having a sequence of SEQ ID NO:2.

5. A recombinant polynucleotide comprising a promoter sequence operably linked to a polynucleotide of claim 3.

6. A cell transformed with a recombinant polynucleotide of claim 5.

7. A method for producing a polypeptide wherein said polypeptide is selected from the group consisting of:
   (i) a polypeptide comprising the amino acid sequence of SEQ ID NO:1; and
   (ii) a naturally-occurring polypeptide having at least 90% sequence identity to the sequence of SEQ ID NO:1 wherein said polypeptide activates ubiquitin, the method comprising:
      a) culturing a cell under conditions suitable for expression of said polypeptide, wherein said cell is transformed with a recombinant polynucleotide, and said recombinant polynucleotide comprises a promoter sequence operably linked to the polynucleotide of claim 2, and
      b) recovering the polypeptide so expressed.

8. A method of claim 7, wherein the polypeptide has the sequence of SEQ ID NO:1.

9. An isolated polynucleotide comprising a sequence selected from the group consisting of:
   a) a polynucleotide sequence of SEQ ID NO:2,
   b) a naturally-occurring polynucleotide sequence having at least 90% sequence identity to the sequence of SEQ ID NO:2, wherein said naturally-occurring polynucleotide encodes a polypeptide that activates ubiquitin,
   c) a polynucleotide sequence complementary to a),
   d) a polynucleotide sequence complementary to b) and
   e) a ribonucleotide equivalent of a)–d).

10. A method for screening a compound for effectiveness in altering expression of a target polynueleotide, wherein said target polynucleotide comprises a sequence of claim 3, the method comprising:
   a) exposing a sample comprising the target polynucleotide to a compound, and
   b) detecting altered expression of the target polynucleotide.

* * * * *